United States Patent
Kumar et al.

(10) Patent No.: US 10,487,347 B2
(45) Date of Patent: Nov. 26, 2019

(54) METHOD OF PRETREATMENT FOR ENHANCED ENZYMATIC HYDROLYSIS

(71) Applicants: INDIAN OIL CORPORATION LIMITED, Mumbai (IN); DEPARTMENT OF BIOTECHNOLOGY, New Delhi (IN)

(72) Inventors: Ravindra Kumar, Haryana (IN); Ruchi Gaur, Haryana (IN); Tirath Raj, Haryana (IN); Manali Kapoor Kakkar, Haryana (IN); Alok Satlewal, Haryana (IN); Ravi Prakash Gupta, Haryana (IN); Deepak Kumar Tuli, Haryana (IN)

(73) Assignees: INDIAN OIL CORPORATION LIMITED, Mumbai (IN); DEPARTMENT OF BIOTECHNOLOGY, New Delhi (IN)

(*) Notice: Subject to any disclaimer, the term of this patent is extended or adjusted under 35 U.S.C. 154(b) by 41 days.

(21) Appl. No.: 15/373,788

(22) Filed: Dec. 9, 2016

(65) Prior Publication Data
US 2017/0166940 A1  Jun. 15, 2017

(30) Foreign Application Priority Data
Dec. 9, 2015 (IN) .......................... 4643/MUM/2015

(51) Int. Cl.
*C12P 19/14* (2006.01)
*C12P 19/02* (2006.01)

(52) U.S. Cl.
CPC .............. *C12P 19/14* (2013.01); *C12P 19/02* (2013.01); *C12P 2201/00* (2013.01); *Y02E 50/16* (2013.01)

(58) Field of Classification Search
CPC ....... C12P 19/02; C12P 2201/00; C12P 19/14; Y02E 50/16
See application file for complete search history.

(56) References Cited

U.S. PATENT DOCUMENTS

| 4,178,861 A | 12/1979 | Vanderhoek et al. |
| 4,826,567 A | 5/1989 | Gratzl |
| 5,049,661 A | 9/1991 | Dilling |
| 2003/0136304 A1 | 7/2003 | Cuculo et al. |
| 2009/0298149 A1 | 12/2009 | Wang et al. |

FOREIGN PATENT DOCUMENTS

WO  2015/063549 A1  5/2015

OTHER PUBLICATIONS

Barbash et al., Cellulose Chem. Technol., 2014, vol. 48, 3-4, p. 345-353, plus one page showing online availablily date Feb. 2013.*
Nikolay et al., Chemistry for Sustainable Development, 2002, vol. 10, p. 297-301.*
Mosier et al., Bioresource Technology, 2005, vol. 96, p. 673-686.*
Zhang et al., Bioresource Technology, 2013, vol. 129, p. 127-134.*
Kobayashi et al., Cellulose, 2012, vol. 19, p. 967-974.*

* cited by examiner

*Primary Examiner* — Kade Ariani
(74) *Attorney, Agent, or Firm* — Maschoff Brennan

(57) ABSTRACT

The present invention discloses a method for producing readily available and hydrolysable polysaccharide-enriched biomass from lignocellulosic biomass while quantitatively retaining carbohydrate and producing fewer amounts of inhibitors. The method includes treating lignocellulosic biomass with an aqueous solution at elevated temperatures in a sequential step using hydrazine hydrate and sodium sulphite. In accordance with the present invention, the biomass may be further treated with a saccharification enzyme consortium to produce fermentable sugars.

13 Claims, 1 Drawing Sheet

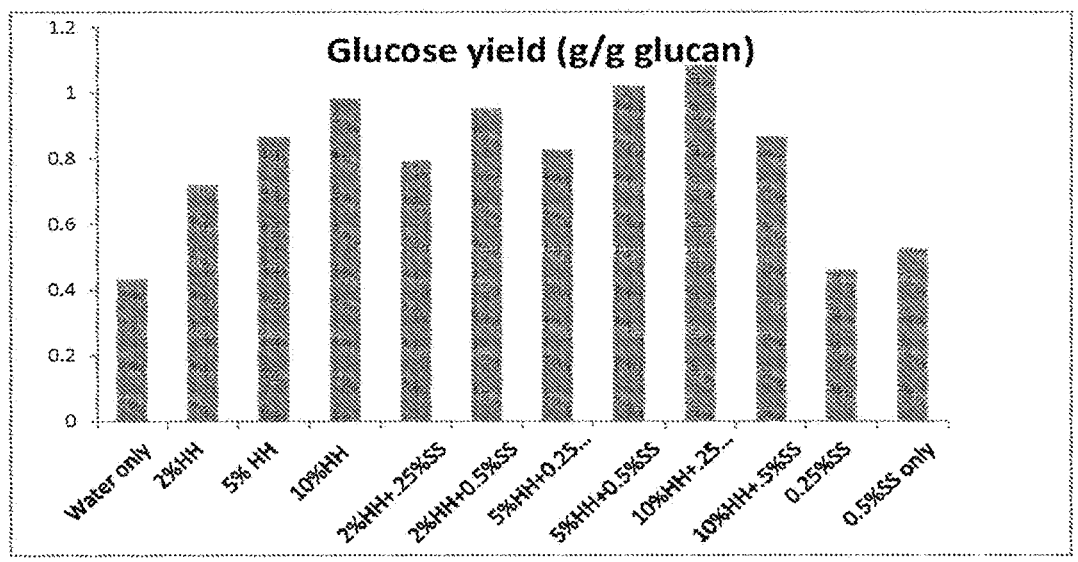

METHOD OF PRETREATMENT FOR ENHANCED ENZYMATIC HYDROLYSIS

FIELD OF THE INVENTION

The present invention relates to a method of pretreatment of biomass, which on saccharification produces fermentable sugars. The method includes treating biomass at elevated temperatures with mixture of di-amine hydrate and sulphur compound so that carbohydrate is quantitatively retained and fewer amounts of inhibitors are formed.

BACKGROUND OF THE INVENTION

Cellulosic and lignocellulosic feedstocks and wastes, such as agricultural residues, wood, forestry wastes, waste from paper manufacture, and municipal and industrial solid wastes, provide a potentially large renewable feedstock for the production of chemicals and fuels as are most abundant and lower in cost. Lignocellulosic biomasses are mainly comprised of cellulose, hemicellulose and lignin. Other non-structural components (phenols, tannins, fats, sterols, sugars, starches, proteins and ashes) of the plant tissue generally accounts for 10% or less of the dry weight of biomass.

Different types of biomass, such as woody plants, herbaceous plants, grasses, aquatic plants, agricultural crops and residues, municipal solid waste and manures, contain varying amounts of cellulose, hemicellulose, lignin, and extractives. Cellulose, the most abundant polysaccharide in all plants and consists mainly of glucose, accounting about 50% of the plant weight. The cellulose chain which form fibrils consists of about 10,000 glucose units. The cellulosic material has a crystal domain separated from the less-ordered, amorphous domain, which allows chemical and biochemical attack, whereas; hemicellulose is a short (100-200 sugar units), highly-branched heteropolymer consisting of predominantly xylose as well as glucose, mannose, galactose, arabinose and other uronic acids. C5 and C6 sugars are linked by 1,3-, 1,6- or 1,4-glucosidic linkages. Often these sugars are acetylated at primary hydroxyl groups. Cellulosic fibrils are embedded in an amorphous matrix network of hemicellulose and lignin, and they serve as glues between the plant cells, providing resistance to biodegradation.

Lignocellulosic biomass (LCB) is the most abundant economically available materials across the world and has been considered as a potent source for ethanol production owing to its easy availability and richness in sugars. These sugars on fermentation produce ethanol. LCB comprise of cellulose, hemicelluloses and lignin besides extractives and ash. Cellulose is a polysaccharide consisting of linear chains of P-(1-4)-D-glucopyranose units. Hemicellulose is a heteropolymer composed of xylan, arabinoxylans, xyloglucan, glucuronoxylan and glucomannan, while lignin is a complex biopolymer of mono-lignols deposited in the cell walls of LCB, which basically provides strength to LCB. LCB need to be pretreated to destruct the biomass cell wall matrix to make it amenable to enzymatic hydrolysis. Subsequently enzymatic hydrolysis using cellulases leads to the production of sugars, which on fermentation results in the production of ethanol.

Pretreatment is the most energy intensive and expensive step for the production of ethanol. Various pretreatment technologies have been explored such as mechanical, steam explosion, AFEX, acid hydrolysis, organosolv, alkaline hydrolysis, lime pretreatment, hot water, and ammonia pretreatment.

Among all, alkali pretreatment is receiving increased interest. The use of an alkali causes the degradation of ester and glycosidic side chains resulting in structural alteration of lignin, cellulose swelling, partial decrystallization of cellulose, and partial solvation of hemicellulose. This facilitates enzyme accessibility and improves cellulose conversion.

For alkaline pretreatment, sodium hydroxide has been extensively studied for many years. It has been shown to disrupt the lignin structure of the biomass, increasing the accessibility of enzymes to cellulose and hemicellulose. Another alkali that has been used for pretreatment of biomass is lime. The limitations associated with alkaline pretreatment are low solid loading, slimy nature of biomass, extensive washing step before enzymatic saccharification.

Lately, green solvents like ionic liquids (ILs) have also come up for dissolving cellulose. But, ILs are expensive and need to be synthesized at lower cost and on a larger scale. Another well used solvent N-methyl morpholine N-oxide (NMMO), also known as the Lyocell solvent is used commercially to produce Tencel fibers. NMMO retains all the advantages of ILs and capable of being recovered up to >99% of the solvent. But, the high temperature required and the cost of NMMO recovery calls for further research to evaluate and improve the economics of its usage for pretreatment of biomass and to integrate it with enzymatic hydrolysis.

Cellulose dissolving mixtures received interest for wood pulping and modification of cellulose to form membranes etc. Jhau and Zhang (2000) reported NaOH-urea solvent system to form cellulose membranes with high tensile strength and storage stability (Polymer Journal, 2000 (32) 866-870).

Amine solvents such as alkanolamines, alkylene diamines and polyalkylene polyamides with pronounced basic properties are capable of delignifying wood or other lignocellulosic raw materials to produce pulp. The associated drawback regarding the use of these compounds involves relatively long reaction times and/or high temperatures and pressures to achieve efficient delignification. However, this limitation could be overcome by the use of compounds like quinonoids or hydroquinonoids, which markedly increased the rate of lignin removal during pulping.

Ammonia based processes like ammonia fiber explosion (AFEX) is another process requiring moderate temperatures. Provision to recover ammonia offers the economic viability to the technique. However, limitations can also be seen in the form of costs during recycle of ammonia and treatment of chemicals that are being used. Also, lignin-carbohydrate complexes are cleaved, and the lignin is deposited on the surfaces of the biomass possibly causing blockage of cellulases to cellulose.

Ammonia and amines penetrate into cellulose crystals, forming crystalline complexes (Clark and Parker 1937; Davis et al. 1943; Klenkova 1967). Hydrazine ($N_2H_4$), the simplest diamine with ammonia-like odor, is known to dissolve cellulose at high temperature and pressure (Kolpak et al. 1977), but it also forms stable complexes with cellulose I and II under ambient temperature and pressure (Lee and Blackwell 1981; Lee et al. 1983). This interaction has been utilized in many industrial processes to enhance accessibility and chemical (Yanai and Shimizu 2006) and enzymatic (Igarashi et al. 2007) susceptibility of cellulose. Hydrazine is recently highlighted as the fuel for a new-type fuel cell, which may contribute to reducing carbon dioxide emission (Asazawa et al. 2007). The major drawbacks of hydrazine are its toxicity and volatility.

In prior art US 20090298149 A1, sulphite/bisulphite has been used for pretreating wood chips for ethanol production. Sulfonation of lignin increases its hydrophilicity, which will promote the enzymatic hydrolysis process. Additionally, it was also mentioned in the prior art U.S. Pat. No. 5,049,661 A, that the addition of some amount of other salts like sulphites, metal chlorides in dilute acid pretreatment improved the enzymatic hydrolysis by delignifying the biomass, which reduce the cellulase amount significantly and in turn produces low amount of inhibitors.

Thus, there is always a need for the efficient pretreatment step which results in production of low amounts of inhibitors in the pretreatment hydrolysate and retains the maximum amount of cellulose in the biomass.

As mentioned in prior art WO 2015063549, in order to hydrolyze the biomass polysaccharides into fermentable sugars, for example by depolymerization, pretreatment processes such as steam explosion, mild acid treatment, strong acid treatment, ammonia treatment, alkali treatment, etc. are employed. Pretreatment is primarily used to make the polysaccharides of lignocellulosic biomass more readily accessible to cellulolytic enzymes. The ideal pretreatment process should be environment-friendly and economically feasible. The pretreatment method will be selected considering the process dependency and cost, as well as process yield and production parameters. Since the major cost of the overall conversion process is due to the biomass feed pretreatment and enzymes, it is necessary to minimize the use of enzymes and obtain the maximum conversion of the carbohydrates to ethanol. For these reasons, a considerable amount of research work has been done for developing means to pretreat the lignocellulosic biomass in such ways that it becomes more accessible to cellulolyic enzymes.

U.S. Pat. No. 4,178,861 A discloses amine based liquor containing a quinone or hydroquinone compound for delignification of lignocellulosic material for manufacture of paper or paperboard. Of the ethanolamines, mono ethanolamine was the preferred compound. Preferred alkylene diamines are those diamino lower alkanes such as ethylene diamines and propylene diamines. Preferred polyalkylene polyamines are derivatives of the lower alkylene diamines such as diethylenetriamine and triethylenetetramine.

U.S. Pat. No. 4,826,567 A discloses a process for the delignification of cellulosic substances wherein hydrazine was added in the third step of treatment. The previous two steps comprised of treating the biomass with acid and hydrogen peroxide. The invention related to a process for the delignification of lignocellulosic substances for preparation of pulps intended for paper manufacture.

N-methylmorpholine-N-oxide (NMMO)/$H_2O$ system developed by Chanzy et al. (Chanzy, H., et al., J Polym Sci: Polym Lett Ed (1979) 17:219-226) has been industrialized for the solvent spinning of cellulose. The product spun by this process is sold under the registered trademarks TENCEL® and COURTAULDS LYOCELL® by Courtaulds Fibres (Holdings) Limited, London, England, United Kingdom. The advantage of this solvent is its ability to attain exceedingly high concentrations of cellulose (e.g. 35% w/w in DP600) and anisotropic solutions, first reported on non-derivatized cellulose. See Chanzy, H. and Peguy, A., J Polym Sci: Polym Phys Ed (1980) 18:1137-1144. However, the NM1\40/$H_2O$ system has significant disadvantages associated with its use, e.g. high temperature required for dissolution; the degradation of cellulose; side-reactions of the solvent itself without an antioxidant (Potthast, A., et al., Holzforschung (2000) 54:101-103); and its high cost.

US2003136304 (A1) discloses a solvent system other than NM1\40-/H2O comprising an amine-based solvent for cellulose. Hydrazine ($NH_2NH_2$)/salt system was found to be an excellent solvent for cellulose. Even at room temperature the combinations of hydrazine and lithium, sodium, and potassium thiocyanate had high dissolution power for cellulose up to 18% w/w maximum unrelated to the polymorph, while the combination with ammonium thiocyanate exhibited a solubility difference among cellulose I, II, and III.

Additionally, in the prior art U.S. Pat. No. 4,178,861 A, it was noticed that the addition of some amount of other salts like quionones, sulphites, metal thiocyanades improved the delignification of lignocellulosic material or improved the cellulose solubilization, with an implication in improved enzymatic hydrolysis. Therefore, search was made to look in the prior art which uses hydrazine along with other salts like sulphites, metal chlorides. The prior art related to this is given below:

In prior art US 20090298149 A1, sulphite/bisulphite has been used for pretreating wood chips for ethanol production. Sulfonation of lignin increases its hydrophilicity, which will promote the enzymatic hydrolysis process. The lignosulfonate in turn has been used as oil field chemicals, pesticide emulsifier, dyeing and finishing auxiliaries for textile, which can be obtained from the concentrated sulfite pretreated solution. In industrial practice for more than a century, sulfite pulping has been and can be operated over a wide range of pH and temperature. The active reagents in sulphite pretreatment liquor are also depended on the pH of the pretreatment temperature. In the prior art, sulfonation has found to be enhanced enhanced because of the acid or alkaline catalysis.

J. Y. Zhu et al. ("Sulfite Pretreatment (SPORL) for robust enzymatic saccharification of spruce and red pine"; Bioresource Technology 100 (2009) 2411-2418) reports sulfite pretreatment to overcome recalcitrance of lignocellulose for the efficient bioconversion of softwoods.

US 20090298149 A1 describes a method using sulfite pretreatment to overcome recalcitrance of lignocellulose (SPORL). More specifically, it relates to a sulfite-based chemical process for pretreating biomass in solutions to reduce access barriers of enzymes to the lignocellulose, resulting in the efficient conversion through enzymatic saccharification.

US 2009/0298149 A1 discloses a method using sulphite-based pretreatment to overcome recalcitrance of lignocelluloses (SPORL). More, specifically, it relates to a sulphite-based chemical process for pretreating biomass in solutions to reduce access barriers of enzymes to the lignocelluloses, resulting in the efficient conversion through enzymatic saccharification.

There is also need in the art to produce ethanol from ligno-cellulosic biomass (LCB) involving the steps of pretreatment, enzymatic hydrolysis followed by fermentation. Particularly, there is also need in the art for a process of pretreatment by which has beneficial effects in the subsequent enzymatic hydrolysis as very low amounts of inhibitors are generated in the pretreatment and high amounts of sugars are released during enzymatic hydrolysis than the methods disclosed in the prior art.

One of the major challenges of biomass pretreatment is to maximize the extraction or chemical neutralization of the lignin, while minimizing the loss of carbohydrate (cellulose plus hemicellulose) via low-cost, efficient processes.

One of the major challenges of biomass pretreatment is to maximize the extraction or chemical neutralization (with respect to non-productive binding of cellulolytic enzymes)

of the lignin, while minimizing the loss of carbohydrate (cellulose plus hemicellulose) via low-cost, efficient processes. The higher the selectivity, the higher the overall yield of monomeric sugars following combined pretreatment and enzymatic saccharification.

SUMMARY OF THE INVENTION

The present invention provides a method of pretreatment of biomass, which on saccharification produces fermentable sugars. More particularly, the present invention provides a method for producing hydrolysable polysaccharides-enriched biomass which comprises of treating biomass with aqueous mixture of di-amine hydrate and sulphur compound and removing hydrolysate from end product to obtain residues of hydrolysable polysaccharides-enriched biomass.

According to one embodiment of the present invention, the method further comprising of treating the residues of hydrolysable polysaccharides-enriched biomass with water or other organic solvent to remove lignin.

According to preferred embodiment of the present invention, the biomass is suspended in the aqueous mixture of di-amine hydrate and sulphur compound.

According to preferred embodiment of the present invention, the biomass is treated with aqueous mixture of di-amine hydrate and sulphur compound at elevated temperature.

According to preferred embodiment of the present invention, the treatment of biomass with aqueous mixture of di-amine hydrate and sulphur compound is done at temperature ranging between 80-20° C. for about 5 minutes to 4 hours.

According to preferred embodiment of the present invention, in the aqueous mixture of di-amine hydrate and sulphur compound, the di-amine hydrate is present in range of 1-99% (w/w) and the sulphur compound is present in range of 0.1-10% (w/w).

According to preferred embodiment of the present invention, the di-amine hydrate is selected from hydrazine hydrate.

According to preferred embodiment of the present invention, the sulphur compound is selected from sulphur dioxide, bisulphate, sodium sulfide and sodium sulfite.

According to preferred embodiment of the present invention, the sulphur compound is selected from sodium sulfite.

According to preferred embodiment of the present invention, the biomass is lignocellulosic biomass.

According to preferred embodiment of the present invention, the biomass is shredded to reduce particle size from 1 mm to 20 mm.

According to preferred embodiment of the present invention, the biomass is selected from cotton stalk, mustard stalk, wheat stalk, wheat straw and rice straw.

According to another embodiment of the present invention, the method further comprising of enzymatic saccharification of the hydrolysable polysaccharides-enriched biomass by contacting it with saccharification enzyme consortium to produces fermentable sugars.

According to one embodiment, the present invention discloses a method for producing readily available and hydrolysable polysaccharide-enriched biomass from lignocellulosic biomass while quantitatively retaining carbohydrate and producing fewer amounts of inhibitors. The method includes treating lignocellulosic biomass with an aqueous solution at elevated temperatures in a sequential step using hydrazine hydrate and sodium sulphite.

According to another embodiment, the biomass may be further treated with a saccharification enzyme consortium to produce fermentable sugars. These sugars may be subjected to further processing for the production of ethanol.

BRIEF DESCRIPTION OF THE FIGURE(S)

The FIGURE shows enzymatic hydrolysis of wheat straw (solid) obtained after pretreatment under different conditions. The glucose yield has been calculated as a percent of theoretical glucose present in solid residue.

DESCRIPTION OF THE INVENTION

While the invention is susceptible to various modifications and alternative forms, specific embodiment thereof will be described in detail below. It should be understood, however that it is not intended to limit the invention to the particular forms disclosed, but on the contrary, the invention is to cover all modifications, equivalents, and alternative falling within the scope of the invention as defined by the appended claims.

The present invention provides a method for producing hydrolysable polysaccharides-enriched biomass which comprises of treating biomass with aqueous mixture of di-amine hydrate and sulphur compound and removing hydrolysate from end product to obtain residues of hydrolysable polysaccharides-enriched biomass.

According to one embodiment of the present invention, the method further comprising of treating the residues of hydrolysable polysaccharides-enriched biomass with water or other organic solvent to remove lignin.

According to preferred embodiment of the present invention, the biomass is suspended in the aqueous mixture of di-amine hydrate and sulphur compound.

According to preferred embodiment of the present invention, the biomass is treated with aqueous mixture of di-amine hydrate and sulphur compound at elevated temperature.

According to preferred embodiment of the present invention, the treatment of biomass with aqueous mixture of di-amine hydrate and sulphur compound is done at temperature ranging between 80-20° C. for about 5 minutes to 4 hours.

According to preferred embodiment of the present invention, in the aqueous mixture of di-amine hydrate and sulphur compound, the di-amine hydrate is present in range of 1-99% (w/w) and the sulphur compound is present in range of 0.1-10% (w/w).

According to preferred embodiment of the present invention, the di-amine hydrate is selected from hydrazine hydrate.

According to preferred embodiment of the present invention, the sulphur compound is selected from sulphur dioxide, bisulphate, sodium sulfide and sodium sulfite.

According to preferred embodiment of the present invention, the sulphur compound is selected from sodium sulfite.

According to preferred embodiment of the present invention, the biomass is lignocellulosic biomass.

According to preferred embodiment of the present invention, the biomass is shredded to reduce particle size from 1 mm to 20 mm.

According to preferred embodiment of the present invention, the biomass is selected from cotton stalk, mustard stalk, wheat stalk, wheat straw and rice straw.

According to another embodiment of the present invention, the method further comprising of enzymatic faccharification of the hydrolysable polysaccharides-enriched biomass by contacting it with saccharification enzyme consortium to produces fermentable sugars.

In the present invention, varieties of biomasses are treated with sodium sulphite and hydrazine hydrate mixture at elevated temperatures. The aqueous solution of sodium sulphite and hydrazine hydrate is used to produce carbohydrate-enriched biomass that is highly susceptible to enzymatic saccharification, producing very high yields of fermentable sugars (glucose, as well as xylose) for bioconversion to target products (e.g., ethanol, value-added chemicals and fuels). Surprisingly, the use of these streams in the present disclosure resulted in significantly improved lignin fragmentation and extraction and high carbohydrate retention resulting in very substantial cost reduction of the biomass pretreatment step.

Hydrazine monohydrate is a strong base and is reactive to cleave ester groups of preferentially acetates similarly to other basic nucleophiles. The present invention reports that the mixture of hydrazine and sulphite further improves the sugar recovery by increasing the enzymatic hydrolysis. In the present invention, biomass is pretreated using only hydrazine, only sodium sulphite or a combination of both. In addition, the current process produced low amounts of inhibitors in the pretreatment hydrolysate and retained maximum amount of cellulose in the biomass.

In accordance with the present invention, the method of producing hydrolysable polysaccharides-enriched lignocellulosic biomass comprising:
(a) providing biomass;
(b) suspending the biomass of (a) in an aqueous mixture of hydrazine hydrate and sodium sulphite (ranging from 1-99% and 0.1-10% respectively);
(c) heating the biomass suspension to a temperature of about 80-200° C. more preferably from 120-180° C. for about 5 minutes to about 4 hours more preferably 10 to 80 minutes; and
(d) removing biomass pretreatment hydrolysate.

Lignocellulosic biomass feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of cellulose, hemicellulose, pectins and lignin are generally treated by a variety of chemical, mechanical and enzymatic means to release primarily hexose and pentose sugars, which can then be fermented to useful products.

In another embodiment the invention provides a method of fragmentation of polysaccharides from lignocellulosic biomass to produce an improved biomass, the method comprising the steps of:
(a) providing:
1) lignocellulosic biomass;
2) aqueous solution of hydrazine and sodium sulphite in water (ranging from 1-99% and 0.110% respectively); and
(b) contacting said biomass with the aqueous solution of hydrazine hydrate and sodium sulphite to form a slurry;
(c) placing the slurry in a sealed pressure vessel whereby the mixture of (b) is heated at a temperature of about 100° C. to about 200° C. for about 10 to 60 minutes;
(d) removing the liquid hydrolysate of (c) by filtration; and
(e) washing the residual biomass with water, whereby substantially pretreated biomass is produced.

EXAMPLES

The following examples are illustrative of the invention but not to be construed to limit the scope of the present invention.

Example 1. Pretreatment with Only Water 100 g of shredded biomass (wheat straw) was taken in high pressure reactor (HPR) unit. The biomass was suspended in water making the total volume of mixture to 1 L. The reaction was allowed to proceed for 30 min at 150° C. and 300 RPM, after which cooling commenced. The total solid content was estimated and the slurry was filtered to obtain xylose rich hydrolyzate and cellulose rich residue.

The pretreated mixture of wheat straw was then filtered through muslin cloth and residual biomass was washed by distilled water till pH became nearly 7. The hydrolysate (liquid part) if acidic was neutralized by using $CaCO_3$ and using HCl if alkaline. Sugars and inhibitors concentration in xylose rich hydolyzate received after pretreatment were measured by HPLC (Waters, USA) with refractive index detector following NREL protocol. The column used for sugar analysis was Aminex HPX-87P maintained at 75° C. and milli-Q water was used as mobile phase at 0.6 ml/min. Inhibitors were analyzed using Biorad Aminex HPX-87H column at 50° C., 0.008N $H_2SO_4$ at flow rate of 0.6 ml/min as mobile phase and using UV detector at 280 nm. Both the columns were equipped with suitable guard columns. The concentration of inhibitors and monomeric sugars obtained are given in Table 1.

Enzymatic Saccharification

The residues obtained from pretreated biomass were washed with water and equilibrated using 0.05 M sodium citrate buffer (pH 4.8). 2 gm of pretreated residues (dry basis) was taken in a 250 ml stoppered conical flask. 100 11.1 of 2% sodium azide solution (to prevent microbial contamination) and sodium citrate buffer (0.05 M, pH 4.8) were added to make the final volume of 20 ml. The content of flask was placed in a shaking incubator at 50° C. and 175 rpm for 30 min and 10 Filter Paper unit (FPU) of Celic-Ctech3 (Novozymes, India) per gram of pretreated biomass was added. Sample aliquots of 200 ul were taken periodically after 2, 4, 6, 24 and 48 h and centrifuged at 10,000×g for 10 min and analyzed for individual sugars (cellobiose, glucose and xylose) in the supernatant using HPLC as described above. The conversions of enzymatic hydrolysis after 48 h are presented in Table 13. Hydrolysis efficiency has been calculated as percentage of glucose obtained w.r.t theoretical glucose present in the pretreated wheat straw and shown in FIG. 1.

TABLE 1

Pretreatment condition, concentration of monomeric sugars and toxins in acid hydrolysate and chemical composition of pretreated wheat straw (PTWS).

| Condition | Solid | Components of hydrolysate (g/L) | | | | | | Chemical composition (%) | | | |
|---|---|---|---|---|---|---|---|---|---|---|---|
| Water (%) | content | Cellobiose | Glucose | Xylose | Acetic acid | HMF | Furfural | Glucan | Xylan | Lignin | Ash |
| 100 | 87.6 | 0.00 | 0.09 | 0.33 | 0.71 | 0.00 | 0.00 | 43.6 | 27.78 | 26.01 | 3.95 |

Enzymatic saccharification of the solid residue was performed as described in Example 1 and conversion at 48 h is reported in Table 13.

Example 2. Pretreatment with 2% Hydrazine Hydrate 100 g of shredded biomass (wheat straw) was taken in high pressure reactor (HPR) unit. Aqueous solution of hydrazine hydrate to a final concentration of 2% (w/w) was added to make the volume up to 1 L. The reaction was allowed to proceed for 30 min at 150° C. and 300 RPM, after which cooling commenced. The total solid content was estimated and the slurry was filtered to obtain xylose rich hydrolyzate and cellulose rich residue.

The hydrolysate was processed for sugar and inhibitor analysis using HPLC as described in Example 1. The concentration of inhibitors and monomeric sugars obtained are given in Table 2. Enzymatic saccharification of the solid residue was performed as described in Example 1 and conversion at 48 h is reported in Table 13. Hydrolysis efficiency has been calculated as percentage of glucose obtained w.r.t theoretical glucose present in the pretreated wheat straw as shown in FIG. 1.

TABLE 2

Pretreatment condition, concentration of monomeric sugars and toxins in acid hydrolysate and chemical composition of pretreated wheat straw (PTWS).

| Condition | Solid | Components of hydrolysate (g/L) | | | | | | Chemical composition (%) | | | |
|---|---|---|---|---|---|---|---|---|---|---|---|
| HH (%) | content (%) | Cellobiose | Glucose | Xylose | Acetic acid | HMF | Furfural | Glucan | Xylan | Lignin | Ash |
| 2 | 75.4 | 0.07 | 0.17 | 0.39 | 1.10 | 0.00 | 0.00 | 51.07 | 22.75 | 14.03 | 5.07 |

Example 3. Pretreatment with 5% Hydrazine Hydrate 100 g of shredded biomass (wheat straw) was taken in high pressure reactor (HPR) unit. Aqueous solution of hydrazine hydrate to a final concentration of 5% (w/w) was added to make the volume up to 1 L. The reaction was allowed to proceed for 30 min at 150° C. and 300 RPM, after which cooling commenced. The total solid content was estimated and the slurry was filtered to obtain xylose rich hydrolyzate and cellulose rich residue.

The hydrolysate was processed for sugar and inhibitor analysis using HPLC as described in Example 1. The concentration of inhibitors and monomeric sugars obtained are given in Table 3. Enzymatic saccharification of the solid residue was performed as described in Example 1 and conversion at 48 h is reported in Table 13. Hydrolysis efficiency has been calculated as percentage of glucose obtained w.r.t theoretical glucose present in the pretreated wheat straw as shown in FIG. 1.

TABLE 3

Pretreatment condition, concentration of monomeric sugars and toxins in acid hydrolysate and chemical composition of pretreated wheat straw (PTWS).

| Condition | Solid | Components of hydrolysate (g/L) | | | | | | Chemical composition (%) | | | |
|---|---|---|---|---|---|---|---|---|---|---|---|
| HH (%) | content (%) | Cellobiose | Glucose | Xylose | Acetic acid | HMF | Furfural | Glucan | Xylan | Lignin | Ash |
| 5 | 70.61 | 0.10 | 0.17 | 0.44 | 0.89 | 0.00 | 0.00 | 54.55 | 24.51 | 15.37 | 4.8 |

Example 4. Pretreatment with 10% Hydrazine Hydrate 100 g of shredded biomass (wheat straw) was taken in high pressure reactor (HPR) unit. Aqueous solution of hydrazine hydrate to a final concentration of 10% (w/w) was added to make the volume up to 1 L. The reaction was allowed to proceed for 30 min at 150° C. and 300 RPM, after which cooling commenced. The total solid content was estimated and the slurry was filtered to obtain xylose rich hydrolyzate and cellulose rich residue.

The hydrolysate was processed for sugar and inhibitor analysis using HPLC as described in Example 1. The concentration of inhibitors and monomeric sugars obtained are given in Table 4. Enzymatic saccharification of the solid residue was performed as described in Example 1 and conversion at 48 h is reported in Table 13. Hydrolysis efficiency has been calculated as percentage of glucose obtained w.r.t theoretical glucose present in the pretreated wheat straw as shown in FIG. 1.

TABLE 4

Pretreatment condition, concentration of monomeric sugars and toxins in acid hydrolysate and chemical composition of pretreated wheat straw (PTWS)

| Condition | Solid | Components of hydrolysate (g/L) | | | | | | Chemical composition (%) | | | |
|---|---|---|---|---|---|---|---|---|---|---|---|
| HH (%) | content (%) | Cellobiose | Glucose | Xylose | Acetic acid | HMF | Furfural | Glucan | Xylan | Lignin | Ash |
| 10 | 75.0 | 0.00 | 0.25 | 0.60 | 1.05 | 0.00 | 0.00 | 53.24 | 22.93 | 15.10 | 4.5 |

Example 5. Pretreatment with 2% Hydrazine Hydrate and 0.25% Sodium Sulfite 100 g of shredded biomass (wheat straw) was taken in high pressure reactor (HPR) unit. Aqueous solution of hydrazine hydrate and sodium sulfite to a final concentration of 2% (w/w) and 0.25% (w/w) was added to make the volume up to 1 L. The reaction was allowed to proceed for 30 min at 150° C. and 300 RPM, after which cooling commenced. The total solid content was estimated and the slurry was filtered to obtain xylose rich hydrolyzate and cellulose rich residue. The hydrolysate was processed for sugar and inhibitor analysis using HPLC as described in Example 1. The concentration of inhibitors and monomeric sugars obtained are given in Table 5.

Enzymatic saccharification of the solid residue was performed as described in Example 1 and conversion at 48 h is reported in Table 13. Hydrolysis efficiency has been calculated as percentage of glucose obtained w.r.t theoretical glucose present in the pretreated wheat straw as shown in FIG. 1.

TABLE 5

Pretreatment condition, concentration of monomeric sugars and toxins in acid hydrolysate and chemical composition of pretreated wheat straw (PTWS).

| Condition | Solid | Components of hydrolysate (g/L) | | | | | | Chemical composition (%) | | | |
|---|---|---|---|---|---|---|---|---|---|---|---|
| HH + SS (%) | content (%) | Cellobiose | Glucose | Xylose | Acetic acid | HMF | Furfural | Glucan | Xylan | Lignin | Ash |
| 2.0 + 0.25 | 80.64 | 0.09 | 0.00 | 0.42 | 1.54 | 0.00 | 0.00 | 53.48 | 27.03 | 14.4 | 5.1 |

Example 6. Pretreatment with 2% Hydrazine Hydrate and 0.5% Sodium Sulfite 100 g of shredded biomass (wheat straw) was taken in high pressure reactor (HPR) unit. Aqueous solution of hydrazine hydrate and sodium sulfite to a final concentration of 2% (w/w) and 0.5% (w/w) was added to make the volume up to 1 L. The reaction was allowed to proceed for 30 min at 150° C. and 300 RPM, after which cooling commenced. The total solid content was estimated and the slurry was filtered to obtain xylose rich hydrolyzate and cellulose rich residue. The hydrolysate was processed for sugar and inhibitor analysis using HPLC as described in Example 1. The concentration of inhibitors and monomeric sugars obtained are given in Table 6. Enzymatic saccharification of the solid residue was performed as described in Example 1 and conversion at 48 h is reported in Table 13. Hydrolysis efficiency has been calculated as percentage of glucose obtained w.r.t theoretical glucose present in the pretreated wheat straw as shown in FIG. 1.

TABLE 6

Pretreatment condition, concentration of monomeric sugars and toxins in acid hydrolysate and chemical composition of pretreated wheat straw (PTWS).

| Condition | Solid | Components of hydrolysate (g/L) | | | | | | Chemical composition (%) | | | |
|---|---|---|---|---|---|---|---|---|---|---|---|
| HH + SS (%) | content (%) | Cellobiose | Glucose | Xylose | Acetic acid | HMF | Furfural | Glucan | Xylan | Lignin | Ash |
| 2.0 + 0.5 | 70.56 | 0.08 | 0.13 | 0.50 | 1.50 | 0.00 | 0.00 | 54.76 | 26.50 | 12.70 | 4.47 |

Example 7. Pretreatment with 5% Hydrazine Hydrate and 0.25% Sodium Sulfite 100 g of shredded biomass (wheat straw) was taken in high pressure reactor (HPR) unit. Aqueous solution of hydrazine hydrate and sodium sulfite to a final concentration of 5% (w/w) and 0.25% (w/w) respectively was added to make the volume up to 1 L. The reaction was allowed to proceed for 30 min at 150° C. and 300 RPM, after which cooling commenced. The total solid content was estimated and the slurry was filtered to obtain xylose rich hydrolyzate and cellulose rich residue.

The hydrolysate was processed for sugar and inhibitor analysis using HPLC as described in Example 1. The concentration of inhibitors and monomeric sugars obtained are given in Table 7. Enzymatic saccharification of the solid residue was performed as described in Example 1 and conversion at 48 h is repoted in Table 13. Hydrolysis efficiency has been calculated as percentage of glucose obtained w.r.t theoretical glucose present in the pretreated wheat straw as shown in FIG. 1.

TABLE 7

Pretreatment condition, concentration of monomeric sugars and toxins in acid hydrolysate and chemical composition of pretreated wheat straw (PTWS).

| Condition | Solid | Components of hydrolysate (g/L) | | | | | | Chemical composition (%) | | | |
|---|---|---|---|---|---|---|---|---|---|---|---|
| HH + SS (%) | content (%) | Cellobiose | Glucose | Xylose | Acetic acid | HMF | Furfural | Glucan | Xylan | Lignin | Ash |
| 5.0 + 0.25 | 75.6 | 0.10 | 0.19 | 0.42 | 0.98 | 0.00 | 0.00 | 60.98 | 23.01 | 13.40 | 4.93 |

Example 8. Pretreatment with 5% Hydrazine Hydrate and 0.5% Sodium Sulfite 100 g of shredded biomass (wheat straw) was taken in high pressure reactor (HPR) unit. Aqueous solution of hydrazine hydrate and sodium sulfite to a final concentration of 5% (w/w) and 0.5% (w/w) respectively was added to make the volume up to 1 L. The reaction was allowed to proceed for 30 min at 150° C. and 300 RPM, after which cooling commenced. The total solid content was estimated and the slurry was filtered to obtain xylose rich hydrolyzate and cellulose rich residue.

The hydrolysate was processed for sugar and inhibitor analysis using HPLC as described in Example 1. The concentration of inhibitors and monomeric sugars obtained are given in Table 8. Enzymatic saccharification of the solid residue was performed as described in Example 1 and conversion at 48 h is reported in Table 13. Hydrolysis efficiency has been calculated as percentage of glucose obtained w.r.t theoretical glucose present in the pretreated wheat straw as shown in FIG. 1.

TABLE 8

Pretreatment condition, concentration of monomeric sugars and toxins in acid hydrolysate and chemical composition of pretreated wheat straw (PTWS).

| Condition | Solid | Components of hydrolysate (g/L) | | | | | | Chemical composition (%) | | | |
|---|---|---|---|---|---|---|---|---|---|---|---|
| HH + SS (%) | content (%) | Cellobiose | Glucose | Xylose | Acetic acid | HMF | Furfural | Glucan | Xylan | Lignin | Ash |
| 5.0 + 0.5 | 87.6 | 0.06 | 0.21 | 0.51 | 1.10 | 0.00 | 0.00 | 58.88 | 23.01 | 14.33 | 6.0 |

Example 9. Pretreatment with 10% Hydrazine Hydrate and 0.25% Sodium Sulfite 100 g of shredded biomass (wheat straw) was taken in high pressure reactor (HPR) unit. Aqueous solution of hydrazine hydrate and sodium sulfite to a final concentration of 10% (w/w) and 0.25% (w/w) respectively was added to make the volume up to 1 L. The reaction was allowed to proceed for 30 min at 150° C. and 300 RPM, after which cooling commenced. The total solid content was estimated and the slurry was filtered to obtain xylose rich hydrolyzate and cellulose rich residue.

The hydrolysate was processed for sugar and inhibitor analysis using HPLC as described in Experiment 1. The concentration of inhibitors and monomeric sugars obtained are given in Table 9.

Enzymatic saccharification of the solid residue was performed as described in Example 1 and conversion at 48 h is reported in Table 13. Hydrolysis efficiency has been calculated as percentage of glucose obtained w.r.t theoretical glucose present in the pretreated wheat straw as shown in FIG. 1.

TABLE 9

Pretreatment condition, concentration of monomeric sugars and toxins in acid hydrolysate and chemical composition of pretreated wheat straw (PTWS).

| Condition | Solid | Components of hydrolysate (g/L) | | | | | | Chemical composition (%) | | | |
|---|---|---|---|---|---|---|---|---|---|---|---|
| HH + SS (%) | content (%) | Cellobiose | Glucose | Xylose | Acetic acid | HMF | Furfural | Glucan | Xylan | Lignin | Ash |
| 10 + 0.25 | 76.8 | 0.09 | 0.27 | 0.37 | 0.98 | 0.00 | 0.00 | 53.18 | 23.50 | 11.6 | 6.0 |

Example 10. Pretreatment with 10% Hydrazine Hydrate and 0.5% Sodium Sulfite 100 g of shredded biomass (wheat straw) was taken in high pressure reactor (HPR) unit. Aqueous solution of hydrazine hydrate and sodium sulfite to a final concentration of 5% (w/w) and 0.25% (w/w) respectively was added to make the volume up to 1 L. The reaction was allowed to proceed for 30 min at 150° C. and 300 RPM, after which cooling commenced. The total solid content was estimated and the slurry was filtered to obtain xylose rich hydrolyzate and cellulose rich residue.

The hydrolysate was processed for sugar and inhibitor analysis using HPLC as described in Experiment 1. The concentration of inhibitors and monomeric sugars obtained are given in Table 10.

Enzymatic saccharification of the solid residue was performed as described in Example 1 and conversion at 48 h is reported in Table 13. Hydrolysis efficiency has been calculated as percentage of glucose obtained w.r.t theoretical glucose present in the pretreated wheat straw as shown in FIG. 1.

TABLE 10

Pretreatment condition, concentration of monomeric sugars and toxins in acid hydrolysate and chemical composition of pretreated wheat straw (PTWS).

| Condition | Solid | Components of hydrolysate (g/L) | | | | | | Chemical composition (%) | | | |
|---|---|---|---|---|---|---|---|---|---|---|---|
| HH + SS (%) | content (%) | Cellobiose | Glucose | Xylose | Acetic acid | HMF | Furfural | Glucan | Xylan | Lignin | Ash |
| 10 + 0.5 | 84.56 | 0.09 | 0.26 | 0.38 | 1.22 | 0.00 | 0.00 | 59.47 | 23.93 | 9.83 | 3.87 |

Example 11. Pretreatment with 0.25% Sodium Sulfite 100 g of shredded biomass (wheat straw) was taken in high pressure reactor (HPR) unit. Aqueous solution of 0.25% sodium sulfite was added to make final volume up to 1 L. The reaction was allowed to proceed for 30 min at 150° C. and 300 RPM, after which cooling commenced. The total solid content was estimated and the slurry was filtered to obtain xylose rich hydrolyzate and cellulose rich residue.

The hydrolysate was processed for sugar and inhibitor analysis using HPLC as described in Experiment 1. The concentration of inhibitors and monomeric sugars obtained are given in Table 11.

Enzymatic saccharification of the solid residue was performed as described in Example 1 and conversion at 48 h is reported in Table 13. Hydrolysis efficiency has been calculated as percentage of glucose obtained w.r.t theoretical glucose present in the pretreated wheat straw as shown in FIG. 1.

TABLE 11

Pretreatment condition, concentration of monomeric sugars and toxins in acid hydrolysate and chemical composition of pretreated wheat straw (PTWS).

| Condition | Solid | Components of hydrolysate (g/L) | | | | | | Chemical composition (%) | | | |
|---|---|---|---|---|---|---|---|---|---|---|---|
| SS (%) | content (%) | Cellobiose | Glucose | Xylose | Acetic acid | HMF | Furfural | Glucan | Xylan | Lignin | Ash |
| 0.25 | 89.64 | 0.07 | 0.19 | 0.56 | 1.96 | 0.00 | 0.00 | 44.45 | 31.85 | 18.9 | 6.1 |

Example 12. Pretreatment with 0.5% Sodium Sulfite 100 g of shredded biomass (wheat straw) was taken in high pressure reactor (HPR) unit. Aqueous solution of 0.5% sodium sulfite was added to make final volume up to 1 L. The reaction was allowed to proceed for 30 min at 150° C. and 300 RPM, after which cooling commenced. The total solid content was estimated and the slurry was filtered to obtain xylose rich hydrolyzate and cellulose rich residue.

The hydrolysate was processed for sugar and inhibitor analysis using HPLC as described in Experiment 1. The concentration of inhibitors and monomeric sugars obtained are given in Table 12.

Enzymatic saccharification of the solid residue was performed as described in Example 1 and conversion at 48 h is reported in Table 13. Hydrolysis efficiency has been calculated as percentage of glucose obtained w.r.t theoretical glucose present in the pretreated wheat straw as shown in FIG. 1.

TABLE 12

Pretreatment condition, concentration of monomeric sugars and toxins in acid hydrolysate and chemical composition of pretreated wheat straw (PTWS).

| Condition | Solid | Components of hydrolysate (g/L) | | | | | | Chemical composition (%) | | | |
|---|---|---|---|---|---|---|---|---|---|---|---|
| SS (%) | content (%) | Cellobiose | Glucose | Xylose | Acetic acid | HMF | Furfural | Glucan | Xylan | Lignin | Ash |
| 0.5 | 75.44 | 0.10 | 0.21 | 0.59 | 0.00 | 0.00 | 0.00 | 43.29 | 29.24 | 18.7 | 6.0 |

TABLE 13

The results obtained by enzymatic hydrolysis after 48 hours as described in Examples 1-12.

| S. No | Hydrazine (%) | Sodium sulfite (%) | Solid content (%) | Lignin (%) per 100 g pretreated biomass | Lignin removed (%) | Glucose content in mg/g biomass as obtained by enzymatic hydrolysis |
|---|---|---|---|---|---|---|
| 1 | — | — | 87.60 | 30.00 | — | 232 |
| 2 | 2.0 | — | 75.40 | 14.93 | 40.01 | 365 |
| 3 | 5.0 | — | 70.61 | 15.37 | 42.19 | 557 |
| 4 | 10.0 | — | 75.00 | 15.10 | 39.66 | 520 |
| 5 | 2.0 | 0.25 | 80.64 | 14.4 | 38.13 | 423 |
| 6 | 2.0 | 0.50 | 70.56 | 12.70 | 52.26 | 520 |
| 7 | 5.0 | 0.25 | 75.60 | 13.40 | 46.03 | 561 |
| 8 | 5.0 | 0.50 | 67.76 | 14.33 | 48.26 | 600 |
| 9 | 10.0 | 0.25 | 76.80 | 11.6 | 52.54 | 573 |
| 10 | 10.0 | 0.50 | 84.56 | 9.83 | 55.70 | 513 |
| 11 | — | 0.25 | 89.64 | 18.9 | 16.94 | 226 |
| 12 | — | 0.50 | 75.44 | 18.7 | 15.97 | 226 |
| 13 | Native Wheat straw | | | 18.77 | | |

The invention claimed is:

1. A method for producing hydrolyzable polysaccharides-enriched biomass comprising of: (a) treating biomass with aqueous mixture of hydrazine hydrate and sulphur compound sodium sulfite to obtain a hydrolyzate and end products; and
(b) removing hydrolyzate from end product as obtained in step (a) to obtain residues of hydrolyzable polysaccharides-enriched biomass, wherein the method further comprising of enzymatic saccharification of the hydrolyzable polysaccharides-enriched biomass in step (b) by contacting it with a saccharification enzyme consortium to produce fermentable sugars.

2. The method as claimed in claim 1, further comprising of treating the residues of hydrolyzable polysaccharides-enriched biomass with water or other organic solvent to remove lignin.

3. The method as claimed in claim 1, wherein the biomass is suspended in the aqueous mixture of hydrazine hydrate and sodium sulfite.

4. The method as claimed in claim 1, wherein the biomass is treated with aqueous mixture of hydrazine hydrate and sodium sulfite at between 80-200° C. temperature.

5. The method as claimed in claim 4 wherein the treatment of biomass with aqueous mixture of hydrazine hydrate and sodium sulfite is done at temperature ranging between 80-200° C. for about 5 minutes to 4 hours.

6. The method as claimed in claim 3, wherein in the aqueous mixture of hydrazine hydrate and sodium sulfite, the hydrazine hydrate is present in range of 1-99% (w/w) and the sodium sulfite is present in range of 0.1-10%) (w/w).

7. The method as claimed in claim 1, wherein the biomass is a lignocellulosic biomass.

8. The method as claimed in claim 1, wherein the biomass is shredded to reduce particle size in the range of 1 mm to 20 mm.

9. The method as claimed in claim 1, wherein the biomass is selected from cotton stalk, mustard stalk, wheat straw and rice straw.

10. The method as claimed in claim 2, wherein the biomass is suspended in the aqueous mixture of hydrazine hydrate and sodium sulfite.

11. The method as claimed in claim 10, wherein in the aqueous mixture of hydrazine hydrate and sodium sulfite, the hydrazine hydrate is present in the range of 1-99% (w/w) and the sodium sulfite is present in the range of 0.1-10% (w/w).

12. The method as claimed in claim 4, wherein in the aqueous mixture of hydrazine hydrate and sodium sulfite, the hydrazine hydrate is present in the range of 1-99% (w/w) and the sodium sulfite is present in the range of 0.1-10% (w/w).

13. The method as claimed in claim 2, wherein the biomass is a liguocellulosic biomass.

\* \* \* \* \*